United States Patent [19]

Toshihiro et al.

[11] Patent Number: 5,457,249

[45] Date of Patent: Oct. 10, 1995

[54] PROCESS FOR ISOMERIZING ENDO-FORM OF AROMATIC GROUP-CONTAINING NORBORNENES TO EXO-FORM THEREOF, ISOMER MIXTURE OF AROMATIC GROUP-CONTAINING NORBORNENES AND PROCESS FOR PREPARING SAME, AND ETHYLENE/AROMATIC GROUP-CONTAINING NORBORNE COPOLYMER AND PROCESS

[75] Inventors: Toshihiro Sagane; Yoichiro Tsuji; Yoshihisa Toda, all of Yamaguchi, Japan

[73] Assignee: Mitsui Petrochemical Industries, Ltd., Tokyo, Japan

[21] Appl. No.: 180,811

[22] Filed: Jan. 10, 1994

Related U.S. Application Data

[63] Continuation of Ser. No. 832,703, Feb. 7, 1992, abandoned.

[30] Foreign Application Priority Data

Feb. 12, 1991 [JP] Japan .................. 3-019065
Feb. 12, 1991 [JP] Japan .................. 3-019066

[51] Int. Cl.[6] .................................. C07C 13/00
[52] U.S. Cl. ................... 585/11; 585/12; 585/24; 528/281; 528/282; 528/283
[58] Field of Search ................... 585/11, 12, 24; 528/281, 282, 283

[56] References Cited

U.S. PATENT DOCUMENTS 4,931,520 6/1990 Yamanashi et al. .
5,106,931 8/1990 Sagane et al. .

FOREIGN PATENT DOCUMENTS 0203799 12/1986 European Pat. Off. .
0325060 7/1989 European Pat. Off. .
0362814 4/1990 European Pat. Off. .
0417489 3/1991 European Pat. Off. .
1185307 7/1989 Japan .

OTHER PUBLICATIONS

Chemical Abstracts, vol. 94, No. 9. 2 Mar. 1981, Columbus Ohio, US; Abstract no. 65212F, IDEITSU KOSAN: "exo-Trimethylenenorbornance" P. 683; column 2; & JP 80 72,122, 30 May 1980 abstract.

Primary Examiner—Asok Pal
Attorney, Agent, or Firm—Sherman and Shalloway

[57] ABSTRACT

A process for isomerization of an endo-form of aromatic group-containing norbornenes represented by the following formula (I) to an exo-form which comprises bringing the endo-form into contact with a solid acid catalyst.

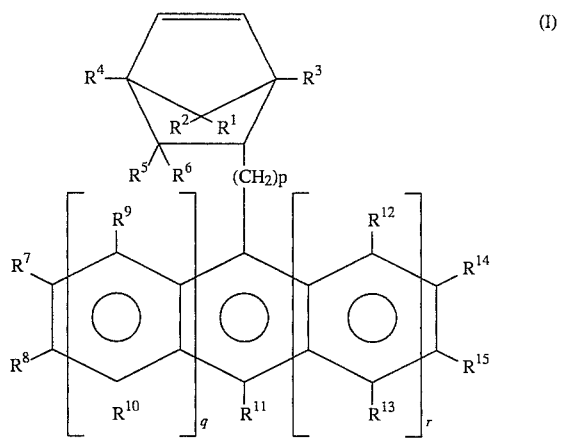

wherein p is 0 or an integer of 1 or more, q and r are each 0, 1 or 2, $R^1$ to $R^{15}$ are each independently hydrogen or halogen atom, aliphatic hydrocarbon group, aromatic hydrocarbon group or alkoxy group, $R^5$ (or $R^6$) are $R^9$ (or $R^7$) may be linked together through an alkylene group of 1–3 carbons or may be directly linked together.

6 Claims, 2 Drawing Sheets

FIG.2

PROCESS FOR ISOMERIZING ENDO-FORM OF AROMATIC GROUP-CONTAINING NORBORNENES TO EXO-FORM THEREOF, ISOMER MIXTURE OF AROMATIC GROUP-CONTAINING NORBORNENES AND PROCESS FOR PREPARING SAME, AND ETHYLENE/AROMATIC GROUP-CONTAINING NORBORNE COPOLYMER AND PROCESS

This application is a continuation of application Ser. No. 07/832,703, filed Feb. 7,1992, now abandoned.

FIELD OF INVENTION

This invention relates to a process for isomerizing endo-form of aromatic group-containing norbornenes to exo-form thereof, an isomer mixture of aromatic group-containing norbornenes and a process for preparing the same, and a cycloolefin random copolymer obtained by random copolymerization of ethylene and said aromatic group-containing norbornenes and a process for preparing the same.

BACKGROUND OF THE INVENTION

As proposed already by way of Japanese Patent L-O-P Publn. No. 178708/1985, Japanese Patent Applns. Nos. 220550/1984, 236828/1984, 236829/1984, 242336/1984 and 95906/1986, it had previously been found by the present applicant that cycloolefin random copolymers obtained by copolymerization of ethylene and cycloolefins such as tetracyclodecene are synthetic resins which are excellent in transparency and also are well balanced among such properties as heat resistance, heat aging resistance, chemical resistance, solvent resistance, dielectric properties and mechanical strength and which exhibit excellent performance in the field of optical materials such as optical memory disk and optical fiber.

Further, the present applicant has found that random copolymers of ethylene and aromatic group-containing norbornenes have also such excellent characteristics as mentioned above.

The aromatic group-containing norbornenes used in preparing such random copolymers as mentioned above may be prepared by Diels-Alder reaction of cyclopentadienes with corresponding olefins. The aromatic group-containing norbornenes are obtained as isomer mixtures containing an endo-form (I-A) and an exo-form (I-B), however, because the cis addition proceeds predominantly, the endo-form (I-A) is mainly formed and very little of the exo-form (I-B) is formed. The isomer mixtures of aromatic group-containing norbornenes obtained by Diels-Alder reaction usually contain the endo-form in an amount of at least 85 mol % or more than 90 mol % in most cases.

The present inventors prosecuted extensive research with the view of improving further heat resistance and mechanical strength of such cycloolefin random copolymers as obtained by copolymerization of ethylene and aromatic group-containing norbornenes, whereupon it has been found that cycloolefin random copolymers obtained by copolymerization of isomer mixtures of aromatic group-containing norbornenes having a relatively large exo-form (I-B) content with ethylene are improved markedly in heat resistance and mechanical strength in comparison with those obtained by copolymerization of isomer mixtures of aromatic group-containing norbornenes having a relative small exo-form (I-B) content with ethylene.

OBJECT OF THE INVENTION

The present invention has been made on the basis of such technical information as accumulated above, and objects of the invention are to provide a process for isomerization of an endo-form (I-A) present in isomer mixtures of aromatic group-containing norbornenes to an exo-form (I-b), provide isomer mixtures of aromatic group-containing norbornenes capable of giving cycloolefin random copolymers having excellent heat resistance and mechanical strength by copolymerization with ethylene and a process for preparing the same, and provide cycloolefin random copolymers excellent in heat resistance and mechanical strength obtained by copolymerization of ethylene and aromatic group-containing norbornenes and a process for preparing the same.

SUMMARY OF THE INVENTION

The process for isomerization of an endo-form (I-A) of aromatic group-containing norbornenes to an exo-form (I-B) according to the present invention is characterized by isomerizing an endo-form (I-A) of an aromatic group-containing norbornene represented by the following general formula (I) to an exo-form (I-B) by contacting the endo-form (I-A) of the aromatic group-containing norbornene with a solid acid catalyst:

wherein p is 0 or an integer of 1 or more, q and r are each 0, 1 or 2, $R^1$ to $R^{15}$ are each independently hydrogen or halogen atom, aliphatic hydrocarbon group, aromatic hydrocarbon group or alkoxy group, $R^5$ (or $R^6$) and $R^9$ (or $R^7$) may be linked together through an alkylene group of 1–3 carbons or may be directly linked together, and $X^1$ represents the portion of the general formula (I).

The isomer mixtures of aromatic group-containing norbornenes according to the present invention are characterized in that the endo-form/exo-form ((I-A)/(I-B)) molar ratio is 80/20 to 0/100.

The process for preparing the isomer mixture of aromatic group-containing norbornenes according to the present invention is characterized in that the endo-form (I-A)/exo-form (I-B) isomer mixtures of aromatic group-containing norbornenes containing the endo-form (I-A) in an amount of not less than 85 mol % are brought into contact with a solid acid catalyst so that the molar ratio ((I-A)/(I-B)) of the endo-form (I-A) to the exo-form (I-B) in said isomer mixture may become 80/20 to 0/100.

The cycloolefin random copolymers of the present invention obtained by random copolymerization of ethylene and aromatic group-containing norbornenes are characterized in that (a) said copolymers are those obtained by random copolymerization of ethylene and the aromatic group-containing norbornenes of the above-mentioned general formula (I) as the isomer mixtures having the endo-form (I-A)/exo-form (I-B) molar ratio ((I-A)/(I-B)) of 80/20 to 0/100, (b) said copolymers contain the structural units derived from ethylene in an amount of 10 to 95 mol %, and the structural units derived from the aromatic group-containing norbornenes in an amount of 90 to 5 mol %, (c) the structural units derived from the aromatic group-containing norbornenes are those represented by the following general formula (II), and (d) said copolymers have an intrinsic viscosity (η), as measured in decalin at 135° C., of 0.05 to 10 dl/g:

wherein p, q, r and $R^1$–$R^{15}$ are as defined above.

The process for preparing the cycloolefin random copolymers by random copolymerization of ethylene and aromatic group-containing norbornenes according to the present invention is characterized by (a) copolymerizing ethylene with the aromatic group-containing norbornenes represented by the above-mentioned general formula (I) as the isomer mixtures having the endo-form (I-A)/exo-form (I-B) molar ratio ((I-A)/(I-B)) of 80/20 to 0/100, (b) in a hydrocarbon solvent or under the conditions where no hydrocarbon solvent exists in the presence of a catalyst composed of a vanadium compound soluble in said hydrocarbon solvent or said aromatic group-containing norbornenes and an organoaluminum.

In accordance with the present invention, there may be obtained cycloolefin random copolymers excellent in heat resistance and mechanical strength.

DETAILED DESCRIPTION OF THE INVENTION

Given below in detail are the preferred embodiments of the present invention, including a process for isomerization of an endo-form of aromatic group-containing norbornenes to an exo-form thereof, isomer mixtures of aromatic group- containing norbornenes and a process for preparing the same, and cycloolefin random copolymers obtained by copolymerization of ethylene and aromatic group-containing norbornenes and a process for preparing the same.

Isomerization

In the process for isomerization of an endo-form of aromatic group-containing norbornenes to an exo-form thereof according to the present invention, the endo-form (I-A) of the aromatic group-containing norbornenes represented by the following general formula (I) is isomerized to the exo-form (I-B) by bringing said endo-form (I-A) into contact with a solid acid:

wherein p is 0 or an integer of 1 or more, q and r are each 0, 1 or 2, $R^1$ to $R^{15}$ are each independently hydrogen or halogen atom, aliphatic hydrocarbon group, aromatic hydrocarbon group or alkoxy group, $R^5$ (or $R^6$) and $R^9$ (or $R^7$) may be linked together through an alkylene group of 1–3 carbon atoms or may be directly linked together, and $X^1$ represents the portion of the general formula (I).

In the formula (I) mentioned above, p is 0 or an integer of at least 1, preferably 0 to 3.

Furthermore, $R^1$–$R^{15}$ each independently represents an atom or a group selected from the group consisting of hydrogen, halogen atom, aliphatic hydrocarbon group, alicyclic hydrocarbon group, aromatic hydrocarbon group and alkoxy group. Examples of the halogen atom include a fluorine atom, a chlorine atom, a bromine atom and an iodine atom. Examples of the aliphatic hydrocarbon groups include an alkyl group of 1 to 6 carbon atoms such as methyl, ethyl, isopropyl, isobutyl, amyl and hexyl. Examples of the alicyclic hydrocarbon groups include cyclohexyl, cyclopropyl, cyclobutyl and cyclopentyl. Examples of the aromatic hydrocarbon groups include an aryl group and an aralkyl group such as phenyl, tolyl, naphthyl, benzyl and phenylethyl. Examples of the alkoxy group include methoxy, ethoxy and propoxy.

In the formula (I) mentioned above, $R^5$ (or R6) and $R^9$ (or $R^7$) may be bonded together through an alkylene group of 1 to 3 carbon atoms, or may be directly bonded together without any intermediate group.

The aromatic group-containing norbornenes used as starting material, that is, an endo-form (I-A) of aromatic group-containing norbornenes, may be obtained by Diels-Alder reaction of cyclopentadienes with corresponding olefins.

The aromatic group-containing norbornenes used in the present invention may include concretely such compounds as will be listed below.

The solid acid used for isomerizing the endo-form (I-A) of such aromatic group-containing norbornenes as mentioned above to exo-form (I-B) thereof includes concretely silica-alumina (composed essentially of $Al_2O_3+SiO_2$), alumina (composed of $Al_2O_3$), zeolite (composed essentially of $Na_2O+SiO_2+Al_2O_3$) and activated clay.

Solid acids other than those exemplified above include concretely such acid metal oxides or acid metal sulfides as $Cr_2O_3$, $P_2O_3$, $TiO_2$, $Al_2O_3\times Cr_2O_3$, $Al_2O_3$ CoO, $Al_2O_3$ MnO, $Cr_2O_3$ $Fe_2O_3$, MoS, $MoS_2$, $CrO_3$, $CrO_2Cl$, $MoO_3$, $V_2O_3$ and $WO_2Cl_2$.

Besides the above-mentioned inorganic compounds, useful solid acids include organic compounds, for example, sulfonic group-containing crosslinked polymers such as Amberlite 15™, Amberlite XE-284™ and Naphyone-H™.

The isomerization reaction of the endo-form (I-A) of the aromatic group-containing norbornenes to the exo-form (I-B) thereof using the solid acid as exemplified above may be carried out by bringing said endo-form (I-A) into contact with said solid acid. In that case, the endo-form (I-A) may be brought into contact directly with the solid acid or may be brought into contact with said solid acid in the presence of an organic solvent.

Such organic solvents as may be used herein include concretely cyclohexane, decalin, hexane, benzene, toluene, carbon tetrachloride and 1,2-dichloroethane.

The contact of the endo-form (I-A) of the aromatic group-containing norbornenes with the solid acid is desirably carried out at a temperature of −5° to 150° C., preferably 0° to 50° C. The contact time employed is about 0.5 to 200 hours, preferably about 1 to 100 hours, though said time varies greatly according to the contact temperature and the concentration of the aromatic group-containing norbornenes used.

The above-mentioned contact between the endo-form (I-A) of the aromatic group-containing norbornenes and the solid acid may be carried out, either batchwise or continuously.

The batchwise operation of the contact of the endo-form (I-A) of the aromatic group-containing norbornenes with the solid acid may be carried out concretely, for example, in the following manner.

To a reactor equipped with a stirrer were added a prescribed amount of an aromatic group-containing norbornene, if necessary, a prescribed amount of an organic solvent and a prescribed amount of a solid acid, and the contents of the reactor were stirred at a prescribed temperature for a prescribed period of time. Thereafter, the reaction mixture was subjected to solid-liquid separation by means of the filtration procedure, and the aromatic group-containing norbornene and the organic solvent in the liquid phase are separated from each other by means of the distillation procedure.

The continuous operation of the contact of the endo-form (I-A) of the aromatic group-containing norbornene with the solid acid may be carried out concretely, for example, by the following procedure.

(i) Using the same reactor as used in the above-mentioned batchwise operation, the aromatic group-containing norbornene or the aromatic group-containing norbornene diluted with the organic solvent continuously fed to the reactor is brought into contact with the solid acid present in the reactor, and the aromatic group-containing norbornene or the aromatic group-containing norbornene diluted with the organic solvent is withdrawn from the reactor.

(ii) To a tower (or a column) packed with the solid acid is added continuously through one end thereof the aromatic group-containing norbornene or that has been diluted with the organic solvent, and the aromatic group-containing norbornene or the dilution product thereof thus contacted with the solid acid is withdrawn continuously from the tower through the other end thereof.

In both procedures (i) and (ii), the aromatic group-containing norbornenes after contact with the solid acid may be separated from the organic solvent by a distillation technique.

By bringing the endo-form (I-A) of the aromatic group-containing norbornenes into contact with the solid acid catalyst, said endo-form (I-A) is isomerized to the endo-form (I-B).

The structure of the endo-form (I-A) and exo-form (I-B) or the endo-form (I-A)/exo-form (I-B) molar ratio in the isomer mixture may be determined by the measurement of hu 1H-NMR or $^{13}$C-NMR.

In practicing the isomerization of the endo-form (I-A) of the aromatic group-containing norbornenes to the exo-form by contact with the solid acid according to the present invention, it is not necessary to use as a starting material the endo-form (I-A) of 100% purity as the starting material, and it is also possible to use a mixture of the endo-form (I-A) and the exo-form (I-B) as the starting material.

Isomer Mixture

The isomer mixture of the aromatic group-containing norbornenes of the general formula (I) of the present invention is a mixture of the endo-form (I-A) and the exo-form (I-B), the molar ratio (I-A)/(I-B) of the endo-form (I-A) to the exo-form (I-B) in the mixture being 80/20 to 0/100, preferably 70/30 to 5/95.

The isomer mixtures of the aromatic group-containing norbornenes having such (I-A)/(I-B) molar ratio as mentioned above cannot be obtained directly from the Diels-Alder reaction of cyclopentadiene with olefins, but may be obtained only when the endo-form (I-A) of said isomer mixture is isomerized to the exo-form (I-B) with the above-mentioned acid catalyzed treatment.

Process for Preparing Isomer Mixture

The isomer mixture of the aromatic group norbornenes having the molar ratio ((I-A)/(I-B)) of the endo-form (I-A) to the exo-form (I-B) of 80/20 to 0/100 may be prepared by bringing an aromatic group-containing norbornene mixture obtained by a Diels-Alder reaction of cyclopentadienes and corresponding olefins and containing the endo-form (I-A) in an amount of at least 85 mol %, at least 90 mol % in most cases, and at least 94 mol % in numerous cases into contact with the above-mentioned solid acid under such conditions as mentioned above, thereby isomerizing the endo-form (I-A) to the exo-form (I-B).

Cycloolefin Random Copolymer

The cycloolefin random copolymers of the present invention are obtained by random copolymerization of ethylene with the aromatic group-containing norbornenes represented by the aforementioned general formula (I), said aromatic group-containing norbornene being isomer mixtures having the molar ratio ((I-A)/(I-B)) of the endo-form (I-A) to the exo-form (I-B) of 80/20 to 0/100.

In the cycloolefin random copolymers of the present invention, the structural units derived from ethylene are present in an amount of 10–95% mol %, preferably 40–85 mol %, and the structural units derived from the aromatic group-containing norbornenes are present in an amount of 90–5 mol %, preferably 60–15 mol %.

In the cycloolefin random copolymers mentioned above, small amounts of other copolymerizable monomers may be copolymerized, so long as said monomers do not hinder the accomplishment of the objects of the invention, therewith, for example, norbornene derivatives other than the aromatic group-containing norbornenes, or α-olefins other than ethylene in an amount of not more than 10 mol % of the structural units derived from the aromatic group-containing norbornenes.

In the cycloolefin random copolymers as mentioned above, the structural units derived from the aromatic group-containing norbornenes have the following structure as represented by the general formula (II):

wherein p, q, r and $R^1$–$R^{15}$ are as defined in the above-mentioned general formula (I).

The ethylene/aromatic group-containing norbornenes copolymers obtained according to the present invention have preferably an intrinsic viscosity (η), as measured in decalin at 135° C., of 0.05 to 10 dl/g.

Preparation of Cycloolefin Random Copolymer

The cycloolefin random copolymers of the present invention may be prepared by copolymerization of the isomer mixture of the aromatic group-containing norbornenes having the molar ratio ((I-A)/(I-B)) of the endo-form (I-A) to the exo-form (I-B) of 80/20 to 0/100 with ethylene in a hydrocarbon solvent or under conditions where no hydrocarbon solvent exists in the presence of a catalyst composed of a vanadium compound soluble in said solvent or aromatic group-containing norbornenes and an organoaluminum compound, preferably a halogen-containing organoaluminum compound.

The hydrocarbon solvents used in the preparation of the cycloolefin random copolymers of the invention include, for example, aliphatic hydrocarbons such as hexane, heptane, octane and kerosine; alicyclic hydrocarbons such as cyclohexane and methylcyclohexane; and aromatic hydrocarbons such as benzene, toluene and xylene.

These solvents as exemplified above may be used, either singly or in combination.

The vanadium compound soluble in the hydrocarbon solvents or aromatic group-containing norbornenes and used for the preparation of the cycloolefin random copolymers of the invention includes concretely vanadium compounds represented by the general formula $VO(OR)_aX_b$ or $V(OR)_cX_d$ wherein R is hydrocarbon, X is halogen, a is $0 \leq a \leq 3$, b is $0 \leq b \leq 3$, c is $0 \leq c \leq 4$, and d is $0 \leq d \leq 4$, or adducts of said vanadium compounds with electron donors.

More particularly, there are used such vanadium compounds as $VOCl_3$, $VO(OC_2H_5)Cl_2$, $VO(OC_2H_5)_2Cl$, $VO(O\text{-iso-}C_3H_7)Cl_2$, $VO(O\text{-n-}C_4H_9)Cl_2$, $VO(OC_2H_5)_3$, $VOBr_2$, $VCl_4$, $VOCl_2$, $VO(O\text{-n-}C_4H_9)_3$ and $VCl_3 \cdot 2OC_9H_{16}OH$.

The electron donors which may be used in the preparation of the vanadium catalyst components include oxygen containing electron donors such as alcohol, phenols, ketone, aldehyde, carboxylic acid, esters of organic or inorganic acid, ether, acid amide, acid anhydride and alkoxysilane, and nitrogen containing electron donors such as ammonia, amine, nitrile and isocyanate.

More particularly, the useful electron donors include alcohols of 1 to 18 carbon atoms such as methanol, ethanol, propanol, pentanol, hexanol, octanol, dodecanol, octadecyl, alcohol, oleyl alcohol, benzyl alcohol, phenylethyl alcohol, cumyl alcohol, isopropyl alcohol and isopropylbenzyl alcohol;

phenol of 6–20 carbon atoms which may have lower alkyl such as phenol, cresol, xylenol, ethylphenol, propylphenol, nonylphenol, cumylphenol and naphthol;

ketones of 3–15 carbon atoms such as acetone, methyl ethyl ketone, methyl isobutyl ketone, acetophenone, benzophenone and benzoquinone;

aldehydes of 2–15 carbon atoms such as acetaldehyde, propionaldehyde, octyl aldehyde, benzaldehyde, tolualdehyde and naphthoaldehyde;

esters of organic acid having 2–30 carbon atoms such as methyl formate, methyl acetate, ethyl acetate, vinyl acetate, propyl acetate, octyl acetate, cyclohexyl acetate, ethyl propionate, methyl butyrate, ethyl valerate, methyl chloroacetate, ethyl dichloroacetate, methyl methacrylate, ethyl dichloroacetate, ethyl crotonate, ethyl cyclohexanecarboxylate, methyl benzoate, ethyl benzoate, propyl benzoate, butyl benzoate, octyl benzoate, cyclohexyl benzoate, phenyl benzoate, benzyl benzoate, methyl toluylate, ethyl toluylate, amyl toluylate, ethyl ethylbenzoate, methyl anisylate, n-butylmaleate, diisobutyl methylmaleate, di-n-hexyl cyclohexenecarboxylate, diethyl nadate, diisopropyl tetrahydrophthalate, diethyl phthalate, diisobutyl phthalate, di-n-butylphthalate, di-2-ethylhexyl phthalate, γ-butyrolactam, δ-valerolactone, coumarin, phthalide and ethylene carbonate;

acid halides of 2–15 carbon atoms such as acetyl chloride, benzoyl chloride, toluic acid chloride and anisic chloride;

ethers of 2–20 carbon atoms such as methyl ether, ethyl ether, isopropyl ether, butyl ether, amyl ether, tetrahydrofuran, anisole and diphenyl ether;

acid amides such as acetic acid amide, benzoic acid amide and toluic acid amide;

amines such as methylamine, ethylamine, diethylamine, tributylamine, piperidine, tribenzylamine, aniline, pyridine, picoline and tetramethylenediamine;

nitriles such as acetonitrile, benzonitrile and tolunitrile; and alkoxysilanes such as ethyl silicate and diphenyldimethoxysilane. These electron donors may be used in combination of two or more.

The organoaluminum compound catalyst components used in the preparation of the cycloolefin random copolymers of the invention have in the molecule at least one Al-carbon bond, for example, organoaluminum compounds represented by the following formula (III)

$$R^1_m Al\ (OR^2)_n H_p X_q \qquad (III)$$

wherein $R^1$ and $R^2$ which may be the same or different are individually hydrocarbons containing usually 1–15 carbon atoms, preferably 1–4 carbon atoms, X is halogen, m is $0 \leq m \leq 3$, n is $0 \leq n < 3$, p is $0 \leq p < 3$, q is $0 \leq q < 3$, and m+n+p+q=3, and alkylated complex products of the group I metals with aluminum represented by the following general formula (IV)

$$M^1 Al\ R^1_4 \qquad (IV)$$

wherein $M_1$ is Li, Na or K, $R^1$ is as defined in the general formula (III).

The organoaluminum compounds represented by the above-mentioned general formula (III) may include those represented by the general formula $R^1_m Al\ (OR^2)_{3-m}$ wherein $R^1$ and $R^2$ are as defined in the above-mentioned general formula (III), and m is preferably $1.5 \leq m < 3$, the general formula $R^1_m AlX_{3-m}$ wherein $R^1$ is as defined in the above-mentioned general formula (III), X is halogen, and m is preferably $0 < m < 3$, the general formula $R^1_m AlH_{3-m}$ wherein $R^1$ is as defined in the above-mentioned general formula (III), and m is preferably $2 \leq m < 3$, and the general formula $R^1_m Al\ (OR^2)_n X_q$ wherein $R^1$ and $R^2$ are as defined in the above-mentioned general formula (III), X is halogen, m is $0 < m \leq 3$, n is $0 \leq n < 3$, q is $0 \leq q < 3$, and m+n+q=3.

The aluminum compounds represented by the general formula (III) include more concretely trialkylaluminum such as triethylaluminum or tributylaluminum;

trialkenylaluminum such as triisopropenylaluminum;

dialkylaluminum alkoxide such as diethylaluminum ethoxide or dibutylaluminum butoxide;

alkylaluminum sesquialkoxide such as ethylaluminum sesquiethoxide or butylaluminum sesquibutoxide and in addition dialkylaluminum halide such as partially alkoxylated alkylaluminum having an average composition represented by $R^1_{2.5}Al(OR^2)_{0.5}$, diethylaluminum chloride, dibutylaluminum chloride or diethylaluminum bromide;

alkylaluminum sesquihalide such as ethylaluminum sesquichloride, butylaluminum sesquichloride or ethylaluminum sesquibromide;

partially halogenated alkylaluminum such as alkylaluminum dihalide, including ethylaluminum dichloride, propylaluminum dichloride or butylaluminum dibromide;

dialkylaluminum hydride such as diethylaluminum hydride or dibutylaluminum hydride;

partially hydrogenated alkylaluminum such as alkylaluminum dihydride, including ethylaluminum dihydride or propylaluminum dihydride; and partially alkoxylated and halogenated alkylaluminum such as ethylaluminumethoxy chloride, butylaluminumbutoxy chloride or ethylaluminumethoxy bromide.

The organoaluminum compound catalyst components used for the preparation of the cycloolefin random copolymer of the invention may also be compounds analogous to those represented by the aforementioned general formula (III), for example, organoaluminum compounds in which at least two aluminum atoms are linked together through an oxygen or nitrogen atom.

Concrete examples of the above-mentioned compounds are as in the following.

Examples of the compounds of the aforementioned formula (IV) may be LiAl(C$_2$H$_5$)$_4$ and LiAl(C$_7$H$_{15}$)$_4$. Of these compounds, particularly useful are alkylaluminum halide, alkylaluminum dihalide or mixtures thereof.

In preparing cycloolefin random copolymers of the invention, the copolymerization reaction of ethylene and the aromatic group-containing norbornenes is desirably carried out by a continuous process. In that case, the concentration of the vanadium compound to be fed to the polymerization reaction system is usually not more than 10 times the concentration of the vanadium compound in the polymerization reaction system, preferably 1 to 7 times, and especially 1 to 5 times.

The ratio of vanadium atoms to aluminum atoms (Al/V) in the polymerization reaction system is at least 2, preferably 2 to 50, and especially 3 to 20.

Usually the vanadium compound and organoaluminum compound to be fed to the copolymerization reaction system are individually diluted with the aforesaid hydrocarbon solvent or aromatic group-containing norbornenes.

In this case, the vanadium compound is desirably diluted to the concentration as defined above, and the organoaluminum compound is diluted to any concentration, for example, not more than 50 times the organoaluminum compound concentration in the polymerization reaction system.

The concentration of the vanadium compound used in the copolymerization reaction system for the preparation of the cycloolefin random copolymers of the invention is usually 0.01–5 mmol/l, preferably, 0.05–3 mmol/l in terms of vanadium atom.

The copolymerization reaction of ethylene and the aromatic group-containing norbornenes as mentioned above may be carried out at a temperature of from −50° to 100° C., preferably from −30° to 80° C., and especially from −20° to 60° C.

The reaction time employed in practicing the copolymerization reaction mentioned above (when the continuous copolymerization is adopted, the reaction time is an average retention time of copolymerization reaction mixture) is usually from 5 minutes to 5 hours, preferably from 10 minutes to 3 hours, though said reaction time varies according to the kind of starting materials to be copolymerized, concentration of the catalyst component used, and the reaction temperature employed. The pressure employed in carrying out the copolymerization reaction is usually exceeding 0 to 50 kg/cm$^2$, preferably exceeding 0 to 20 kg/cm$^2$.

The molar ratio of ethylene/aromatic group-containing norbornenes used in preparing the cycloolefin random copolymers is usually 90/10 to 10/90, preferably 85/15 to 40/60.

In the cycloolefin random copolymers obtained in the manner described above, small amounts of other copolymerizable monomers may be copolymerized therewith, so long as they do not hinder the accomplishment of the objects of the invention, for example, norbornene derivatives other than the aromatic group-containing norbornenes of α-olefins other than ethylene in an amount of not more than 10 mol % of the structural units derived from the aromatic group-containing norbornenes.

By carrying out the copolymerization reaction of ethylene with the aromatic group-containing norbornenes in the manner as mentioned above, there is obtained a solution of a cycloolefin random copolymer in hydrocarbon solvent and, if any, an unreacted cycloolefin solution. The concentration of the cycloolefin random copolymer contained in such copolymer solution is usually 0.5–40% by weight, preferably 2.0–30% by weight, and said copolymer solution contains the soluble vanadium compound component and the organoaluminum compound component, both being the catalyst components.

The solution of the cycloolefin random copolymer of the invention thus obtained is subjected usually to a series of treatment, from de-ashing to pelletizing, thereby giving pellets of the cycloolefin random copolymer.

EFFECT OF THE INVENTION

Making a comparison between the cycloolefin random copolymers of the present invention obtained by copolymerization of isomer mixtures of such aromatic group-containing norbornenes as having the molar ratio ((I-A)/(I-B)) of the endo-form (I-A) to the exo-form (I-B) of 80/20 to 0/100 with ethylene and such cycloolefin random copolymers as may be obtained by copolymerization of isomer mixtures of aromatic group-containing norbornenes containing the endo-form (I-A) in an amount of at least 85 mol % at least 90 mol % in most cases and at least 94 mol % with ethylene, both being the same in the compositions of ethylene and the aromatic group-containing norbornenes, it is found that in the case of the present copolymers, the monomer reactivity ratio of the aromatic group-containing norbornenes in the copolymerization reaction become higher, the glass transition point (Tg) is higher, the heat resistance is excellent, and the mechanical strength is excellent as evidenced by a larger flexural modulus (FM). Accordingly, it becomes possible to reduce the amount of expensive aromatic group-containing norbornenes to be copolymerized by the use of the isomer mixtures of the aromatic group-containing norbornenes of the present invention when the cycloolefin random copolymers having the same glass transition point (Tg) or flexural modulus (FM) are needed.

According to the process for the preparation of cycloolefin random copolymers of the present invention, such cycloolefin random copolymers as illustrated above can be prepared efficiently.

EXAMPLE

The present invention is illustrated below with reference to examples, but it should be construed that the invention is in no way limited to those examples.

Method of Determination

The molar ratio ((I-A)/(I-B)) of the endo-form (I-A) to the exo-form (I-B) of the isomer mixture of 1,4-methano-1,4,4a,9a-tetrahydrofluorene (hereinafter sometimes abbreviated to "MTHF") was calculated on the basis of the integrated intensity ratio of the absorption peak of olefin proton in the spectrum obtained by measurement of $^1$H-NMR (in CDCl$_3$, room temp., based on TMS).

Table 1A and Table 1B individually show the chemical shift of olefin proton obtained by measurement of $^1$H-NMR of MTHF.

Table 1A and Table 1B individually show the chemical shift of carbon obtained by measurement of $^{13}$C-NMR of

MTHF.

TABLE 1 A $^1$H-NMR amd $^{13}$C-NMR chemical shifts (TMS basis)
of 1,4-methano-1,4,4a,9a-tetrahydrofluorene Structure (Endo-form)

σ (ppm)
$^1$H—NMR

| $H^1$ | $H^2$ |
|---|---|
| 5.92 | 5.58 |

$^{13}$C—NMR

| a | b | c | d |
|---|---|---|---|
| 132.89 | 136.24 | 46.82 | 53.67 |
| e | f | g | h |
| 145.00 | 124.05 | 126.14 | 125.68 |
| i | j | k | l |
| 124.24 | 145.58 | 34.53 | 41.76 |
| m | n | — | — |
| 46.51 | 50.60 | — | — |

TABLE 1 B $^1$H-NMR amd $^{13}$C-NMR chemical shifts (TMS basis)
of 1,4-methano-1,4,4a,9a-tetrahydrofluorene Structure (Exo-form)

σ (ppm)
$^1$H—NMR

| H | H |
|---|---|
| 6.06 | 6.17 |

$^{13}$C—NMR

| a | b | c | d |
|---|---|---|---|
| 137.69 | 137.54 | 48.50 | 53.33 |
| e | f | g | h |
| 144.73 | 124.05 | 126.45 | 126.14 |
| i | j | k | l |
| 124.68 | 146.18 | 36.64 | 42.56 |
| m | n | — | — |
| 48.74 | 42.04 | — | — |

Measurement of Softening Temperature

Samples for measurement of softening temperature were obtained by molding the copolymers obtained in examples and comparative examples into a sheet of 1 mm in thickness. The samples thus obtained were individually tested for thermal distortion behavior by means of Thermomechanical Analyzer (TMA) of Du Pont. That is, a quartz needle was placed vertically on the sample and the sample was heated continuously at a rate of 5° C./min while applying a load of 49 g onto the needle. The temperature at which the needle permeated into the sample to the depth of 0.635 mm was taken as a softening temperature. (Hereinafter this temperature is called "TMA softening point".)

Measurement of Flexural Modulus

The measurement of flexural modulus was conducted at 23° C. in accordance with the method of measurement of ASTM D 790.

Measurement of Intrinsic Viscosity

The measurement of intrinsic viscosity was conducted in decalin used as a solvent at a temperature of 135° C.

Referential Example 1

1,4-methano-1,4,4a,9a-tetrahydrofluorene (MTHF) was prepared by Diels-Alder reaction of indene with cyclopentadiene in accordance with the process described in Japanese Patent Publication No. 14910/1971.

The MTHF thus obtained was analyzed by means of $^1$H-NMR to determine the amounts of the endo-form and exo-form. The amounts of the endo-form and exo-form contained were 87 mol % and 13 mol %, respectively.

Results obtained are shown in Table 2.

Referential Example 2

5-Phenyl-bicyclo(2.2.1)hept-2-ene (hereinafter sometimes abbreviated to "Ph-BH") was prepared by Diels-Alder reaction of styrene and cyclopentadiene carried out in the same manner as in Referential Example 1.

The Ph-BH thus obtained was analyzed by means of $^1$H-NMR to determine the amounts of the endo-form and exo-form contained therein. The amounts of the endo-form and exo-form contained were 92 mol % and 8 mol %, respectively.

Results obtained are shown in Table 2.

Example 1

To a 30-liter reactor equipped with a stirring device and a reflux condenser were added 1 liter of MTHF obtained in referential Example 1 and 17 liters of cyclohexane, followed by stirring. To the solution obtained was added 6 kg of zeolite (Zeolam F-7, a product of Tosoh K.K., spherical form, 1.8–2.4 mmφ, $Na_2O.Al_2O_3.2.5\ SiO_2$), and the resulting mixture was stirred at room temperature for 6 hours to carry out isomerization reaction of the endo-form to the exo-form.

After the completion of the reaction, the reaction mixture was filtered to remove the catalyst therefrom, and the cyclohexane solution of MTHF was distilled under reduced pressure (50 mmHg) to remove the cyclohexane therefrom, whereby the isomerized MTHF was obtained.

The MTHF thus obtained was analyzed by means of $^1$H-NMR, whereupon the molar ratio of the endo-form/exo-form was 41/59.

Results obtained are shown in Table 2.

Example 2

The isomerization reaction of MTHF was carried out in the same manner as in Example 1 except that the reaction time was changed to 3 hours.

Results obtained are shown in Table 2.

Example 3

The reaction was carried out in the same manner as in Example 1 except that silica-alumina (Segard OW, a product of Shinagawa Hakurenga K.K., granular form, 0.5–2 mm$\phi$, $Al_2O_3 \cdot mSiO_2 \cdot nH_2O + Al(OH)_3$) was used as a catalyst, the amounts of cyclohexane and the catalyst were changed to 4.0 liters and 3 kg, respectively, and the reaction time was changed to 69 hours. Results obtained are shown in Table 2.

Example 4

The reaction was carried out in the same manner as in Example 1 except that the PhBh obtained in Referential Example 2 was used in place of the MTHF.

Results obtained are shown in Table 2.

Example 5

The reaction was carried out in the same manner as in Example 4 except that the reaction time was changed to 3 hours.

Results obtained are shown in Table 2.

Example 6

The reaction was carried out in the same manner as in Example 4 except that the silica-alumina used in Example 3 was used as a catalyst, and the reaction time was changed to 96 hours.

Results obtained are shown in Table 2.

TABLE 2

| | Abbreviation of aromatic group-containing norbornenes | Isomerization reaction conditions | | | | Isomer composition ratio (%) endo/exo endo: Endo-form (I-A) exo: Exo-form (I-B) |
|---|---|---|---|---|---|---|
| | | Cyclohexane (l) | Aromatic group-containing norbornenes (l) | Kind and amount of solid acid (kg) | Reaction time (h) | |
| Ref. Ex. 1 | MTHF | No isomerization reaction | | | | 87/13 |
| Ex. 1 | MTHF | 17.0 | 1.0 | Zeolite a) 6 | 6 | 41/59 |
| Ex. 2 | MTHF | 17.0 | 1.0 | Zeolite a) 6 | 3 | 57/43 |
| Ex. 3 | MTHF | 4.0 | 1.0 | Silica-alumina b) 3 | 96 | 31/69 |
| Ref. Ex. 2 | Ph—BH | No isomerization reaction | | | | 92/8 |
| Ex. 4 | Ph—BH | 17.0 | 1.0 | Zeolite a) 6 | 6 | 49/51 |
| Ex. 5 | Ph—BH | 17.0 | 1.0 | Zeolite a) 6 | 3 | 35/65 |
| Ex. 6 | Ph—BH | 17.0 | 1.0 | Silica-alumina b) 12 | 96 | 11/89 | a) Product of Tosoh K.K., Tradename: Zeolam F-9, Sherical form, 1.8–2.4 mm$\phi$, $Na_2O \cdot Al_2O_3 \cdot 2.5SiO_2$
b) Product of Shinagawa Hakulenga K.K., Tradename: Segard OW, Granular form, 0.5–2 mm$\phi$, $Al_2O_3 \cdot mSiO_2 \cdot nH_2O. + Al(OH)_3$

Example 7

To a 1-liter glass polymerization reactor equipped with a stirring device were added continuously through the upper portion of the reactor a cyclohexane solution of MTHF obtained in Example 1, a cyclohexane solution of $VO(OC_2H_5)Cl_2$ and a cyclohexane solution of ethylaluminum sesquichloride ($Al(C_2H_5)_{1.5}Cl_{1.5}$) as catalysts so that the concentrations thereof in the reactor may become 60 g/l, 0.5 mmol/l and 4.0 mmol/l, respectively, and ethylene and hydrogen through the upper portion of the reactor at feet rates of 15 liters/hr and 0.5 liter/hr, respectively. On the one hand, the reaction mixture was withdrawn continuously through the upper portion of the reactor so that the total quantity of the polymerization liquid in the reactor may become 1 liter and an average retention time may become 0.5 hours.

The polymerization reaction was carried out at the polymerization temperature maintained at 10° C. by circulating a cooling medium through a cooling jacket provided outside the reactor.

By carrying out the copolymerization reaction under the reaction conditions as mentioned above, a polymerization reaction mixture containing an ethylene/MTHF random copolymer was obtained. The polymerization reaction was stopped by adding small amounts of isopropyl alcohol to the polymerization liquid continuously withdrawn from the upper portion of the reactor. Thereafter, an aqueous solution comprising 1 liter of water, to which 5 ml of concentrated hydrochloric acid had been added, and the polymerization liquid were brought into contact with each other at the proportion of 1:1 with strong stirring by means of a homomixer, thereby migrating the catalyst residue to an aqueous phase. The above-mentioned mixture was allowed to stand and washed twice with distilled water after removal of the aqueous phase, whereby the polymerization liquid was purified and separated.

Subsequently, the polymerization liquid obtained after stopping the reaction was added with strong stirring to a mixer charged with acetone of about 3 times the volume of the polymerization liquid to precipitate the copolymer, which was then separated by filtration from the solution. The copolymer thus obtained as a powder was dispersed in acetone so that the concentration of the copolymer could become about 50 g/l and the resulting mixture was heat treated at the boiling point of acetone for about 2 hours. After the treatment, the copolymer was separated by filtration from the acetone, and was dried under reduced pressure at 120° C. for 24 hours.

Examples 8–14 and Comparative Examples 1–2

Using the starting materials (aromatic group-containing norbornenes), the copolymerization of ethylene and MTHF was carried out under the conditions as shown in Table 3 in the same manner as in Example 7.

Results obtained are shown in Table 4.

Figure 1:
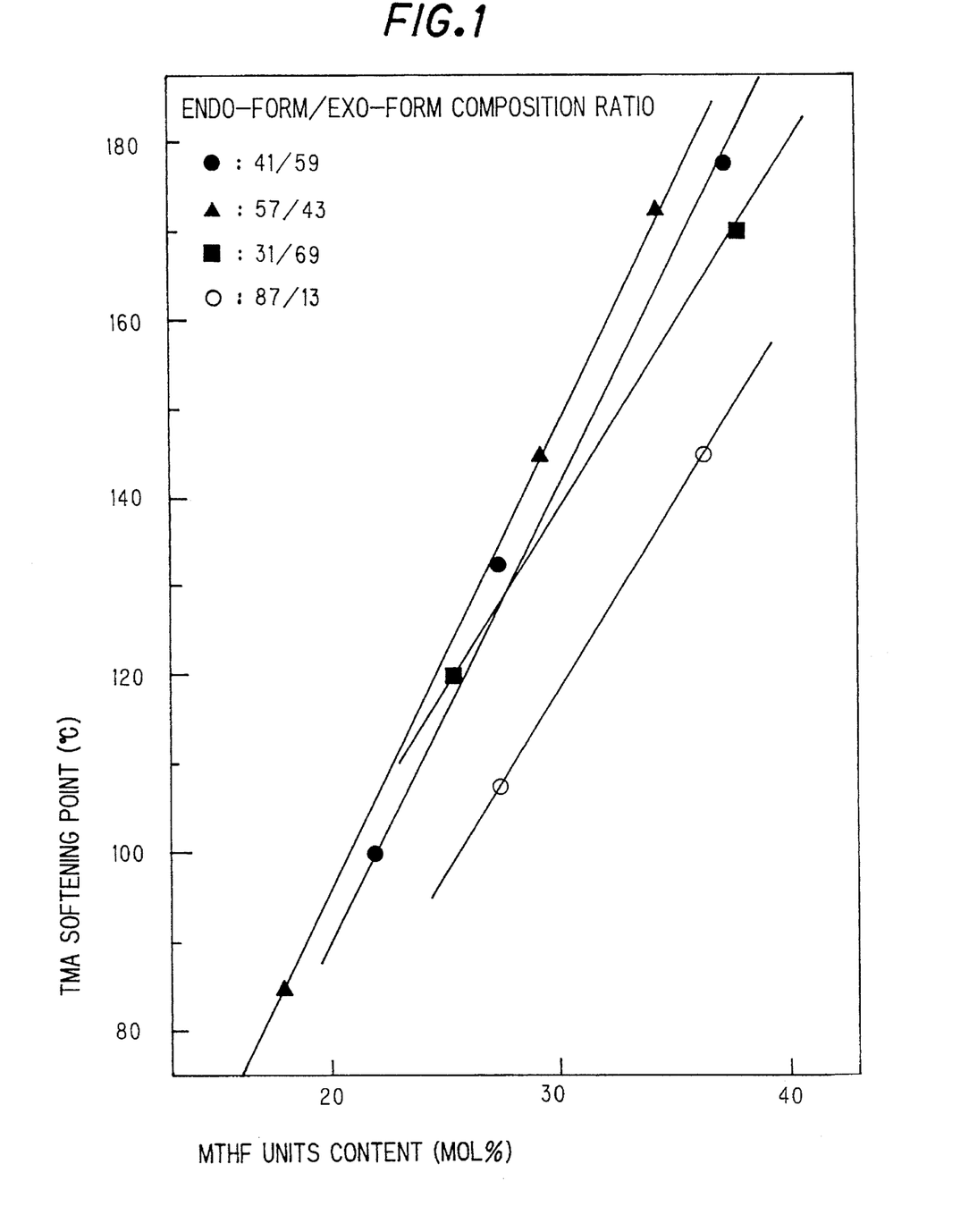
FIG. 1 is a graph showing the relationship between the content (mol %) of the aromatic group-containing norbornene and TMA softening point in the ethylene/aromatic group-containing norbornene copolymers obtained by copolymerization of isomer mixtures of aromatic group-containing norbornenes (MTHF) having varied endo-form/exo-form ratio with ethylene.
Figure 2:
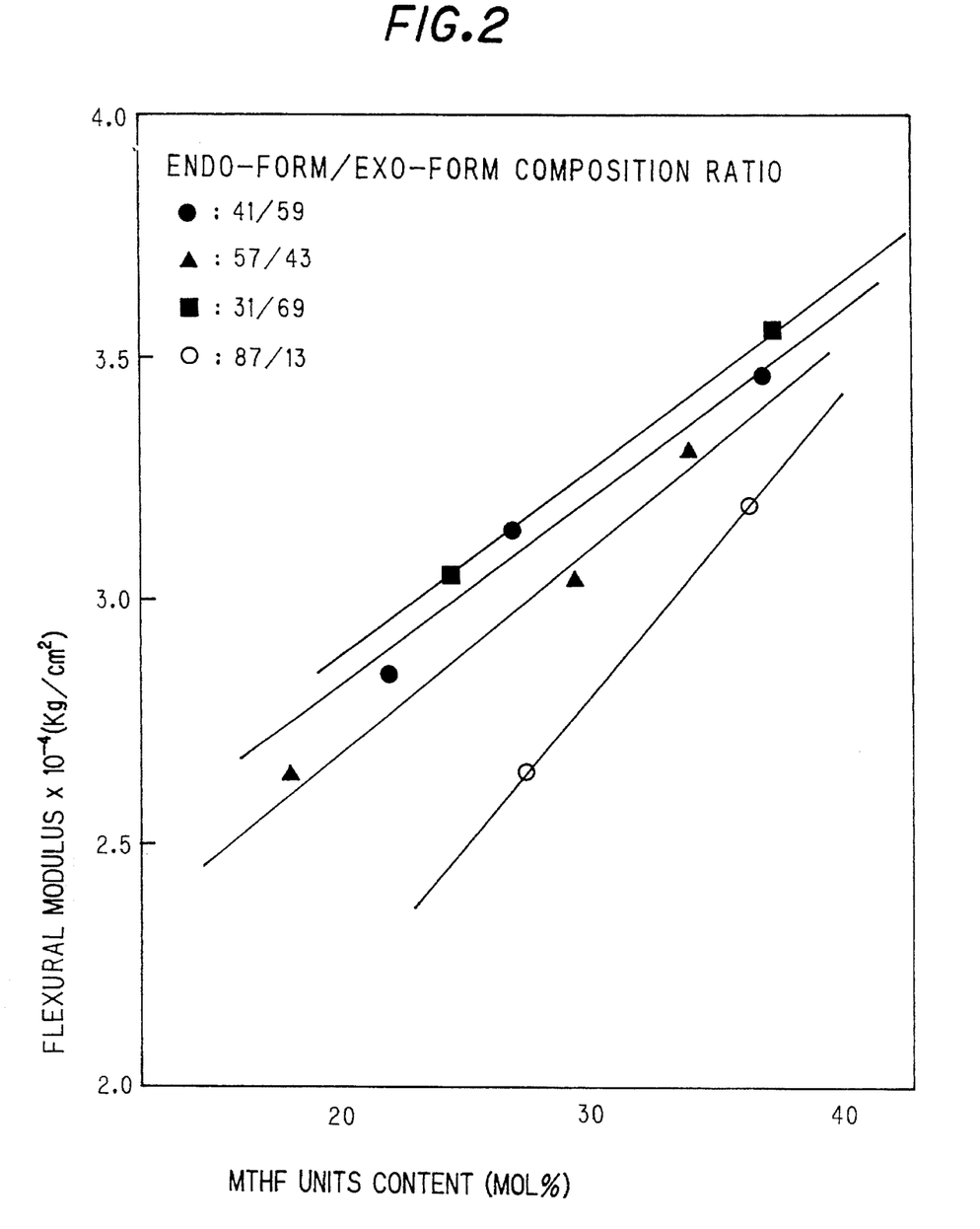
FIG. 2 is a graph showing the relationship between the content (mol %) of the aromatic group-containing norbornene and flexural modulus in the above-mentioned ethylene/aromatic group-containing norbornene (MTHF) copolymers.

FIG. 1 shows the relationship between the aromatic group-containing norbornene content (mol %) and TMA softening point of the ethylene/MTHF copolymer thus obtained, and FIG. 2 shows the relationship between the aromatic group-containing norbornene content (mol %) and flexural modulus (FM) of said copolymer.

TABLE 3

|  | Amount of ethylene fed (l/hr) | MTHF | Endo-form/exo-form (mol %) | Amount fed (g/l) | Amount of H₂ fed (g/l) |
|---|---|---|---|---|---|
| Ex. 7 | 15 | Ex. 1 | 41/59 | 60 | 0.5 |
| Ex. 8 | 30 | Ex. 1 | 41/59 | 60 | 0.5 |
| Ex. 9 | 30 | Ex. 1 | 41/59 | 30 | 1.0 |
| Ex. 10 | 20 | Ex. 2 | 57/43 | 52 | 0.75 |
| Ex. 11 | 30 | Ex. 2 | 57/43 | 52 | 1.0 |
| Ex. 12 | 30 | Ex. 2 | 57/43 | 25 | 2.0 |
| Ex. 13 | 15 | Ex. 3 | 31/69 | 60 | 0.5 |
| Ex. 14 | 30 | Ex. 3 | 31/69 | 60 | 0.5 |
| Comp. Ex. 1 | 35 | Ref. Ex. 1 | 87/13 | 45 | 0.5 |
| Comp. Ex. 2 | 35 | Ref. Ex. 1 | 87/13 | 60 | 0.5 |

The ethylene/MTHF copolymer thus obtained was analyzed by means of $^{13}$C-NMR, whereby the ethylene content in the copolymer was 63.0 mol %. An intrinsic viscosity ($\eta$)

TABLE 4

|  | Yield of polymer (g/l) | Polymer composition (mol %) | | (Endo-form/exo-form of MTHF) | Physical properties of polymer | | |
|---|---|---|---|---|---|---|---|
|  |  | Ethylene | MTHF |  | Intrinsic viscosity ($\eta$) (dl/g) | TMA Softening point (°C.) | Flexural modulus (kg/cm²) |
| Ex. 7 | 33 | 63.0 | 37.0 | (40/60) | 0.41 | 178 | 34900 |
| Ex. 8 | 51 | 72.7 | 27.3 | (41/59) | 0.55 | 130 | 31800 |
| Ex. 9 | 43 | 77.9 | 22.1 | (40/60) | 0.48 | 99 | 28300 |
| Ex. 10 | 46 | 65.4 | 34.6 | (58/42) | 0.40 | 173 | 33500 |
| Ex. 11 | 53 | 70.5 | 29.5 | (57/43) | 0.40 | 145 | 30900 |
| Ex. 12 | 43 | 82.2 | 17.8 | (57/43) | 0.36 | 84 | 26300 |
| Ex. 13 | 41 | 62.7 | 37.3 | (29/71) | 0.41 | 164 | 35700 |
| Ex. 14 | 59 | 74.4 | 25.6 | (31/69) | 0.59 | 119 | 30800 |
| Comp. Ex. 1 | 45 | 72.4 | 27.6 | (88/12) | 0.61 | 108 | 26500 |
| Comp. Ex. 2 | 42 | 63.7 | 36.3 | (87/13) | 0.53 | 145 | 32100 | and TMA softening point of this copolymer were 0.41 dl/g and 178° C., respectively.

Results obtained are shown in Table 4.

The molar ratio of the endo-form to the exo-form of MTHF unit contained in the copolymer thus obtained was measured by means of $^{13}$C-NMR, whereupon the endo-form/exo-form ratio was 40/60, and practically no change was observed in this value of the ratio before and after polymerization.

Examples 15–17 and Comparative Examples 3

Using the starting materials (Ph-BH) as shown in Table 5, the copolymerization of ethylene and Ph-BH was carried out in the same manner as in Example 7 under the conditions as shown in Table 5.

It is understood that the copolymers obtained in Examples 15–17 by using Ph-BH having a relatively high exo-form content are improved in both TMA softening point and flexural modulus in comparison with the copolymer obtained in Comparative Example 3.

TABLE 5

| | Amount of ethylene fed (l/hr) | Ph—BH Example number | Endo-form/exo-form (mol %) | Amount fed (g/l) | Amount of $H_2$ fed (g/l) |
|---|---|---|---|---|---|
| Ex. 15 | 35 | Ex. 4 | 41/59 | 60 | 0.5 |
| Ex. 16 | 35 | Ex. 5 | 41/59 | 60 | 0.5 |
| Ex. 17 | 35 | Ex. 6 | 41/59 | 60 | 0.5 |
| Comp. Ex. 3 | 35 | Ref. Ex. 2 | 92/8 | 60 | 0.5 |

TABLE 6

| | Yield of polymer (g/l) | Polymer composition (mol %) | | | Physical properties of polymer | | |
|---|---|---|---|---|---|---|---|
| | | Ethylene | Ph—BH | (Endo-form/exo-form of Ph—BH) | Intrinsic viscosity ($\eta$) (dl/g) | TMA Softening point (°C.) | Flexural modulus (kg/cm²) |
| Ex. 15 | 49 | 69.1 | 30.9 | (49/51) | 0.59 | 118 | 27100 |
| Ex. 16 | 52 | 71.7 | 28.3 | (34/66) | 0.61 | 113 | 26900 |
| Ex. 17 | 44 | 69.0 | 31.0 | (12/88) | 0.58 | 109 | 26500 |
| Comp. Ex. 3 | 43 | 70.5 | 29.5 | (92/8) | 0.63 | 97 | 23400 |

What is claimed is:

1. A cycloolefin random copolymer comprising structural units derived from ethylene and structural units derived from an aromatic group-containing norbornene wherein

(a) said aromatic group-containing norbornene is represented by the following formula (I) and is an isomer mixture having a molar ratio of an endo-form (I-A) to an exo-form (I-B) ((I-A/I-B)) of 80/20 to 0/100, (b) said structural units derived from ethylene are present in an amount of from 10 to 95 mol %, and said structural units derived from the aromatic group-containing norbornene are present in an amount of from 90 to 5 mol %,

(c) the structural units derived from the aromatic group-containing norbornene are those represented by the following general formula (II), and (d) said copolymer has an intrinsic viscosity ($\eta$), as measured in decalin at 135° C., of 0.05 to 10 dl/g, Endo-form (I-A)

Exo-form (I-B)

wherein p is 0 or an integer of 1 or more, q and r are each independently 0, 1 or 2, $R^1$ to $R^{15}$ are each, independently hydrogen or halogen atom, aliphatic hydrocarbon group, aromatic hydrocarbon group or alkoxy group, or alternatively $R^5$ (or $R^6$) and $R^9$ (when q is not 0) or ($R^7$) may be linked together through an alkylene group of 1–3 carbons or directly linked together, and $X^1$ represents the portion of the general formula (I), wherein p, q, r and $R^1$–$R^{15}$ are as defined above.

2. The cycloolefin random copolymer according to claim 1 wherein said copolymer comprises structural units derived from ethylene in an amount of 40 to 85 mol %, and structural units derived from the aromatic group-containing norbornene in an amount of 60 to 15 mol %.

3. The cycloolefin random copolymer according to claim 1 wherein the isomer mixture has a molar ratio of endo-form (I-A) to exo-form (I-B) ((I-A/(I-B)) of 70/30 to 5/95.

4. The cycloolefin random copolymer according to claim 1 wherein said copolymer contains structural units derived from ethylene in an amount from about 63 mol % to about 82 mol % and structural units derived from the aromatic group-containing norbornene in an amount from about 37 mol % to about 18 mol %.

5. A process for using an isomer mixture of an aromatic group-containing norbornene containing at least 20 mol % of exo-form isomer to prepare a cycloolefin random copolymer, which comprises (a) copolymerizing ethylene and the aromatic-group-containing norbornene represented by the general formula (I)

wherein p is 0 or an integer of 1 or more, q and r are each independently 0, 1 or 2, $R^1$ to $R^{15}$ are each, independently hydrogen or halogen atom, aliphatic hydrocarbon group, aromatic hydrocarbon group or alkoxy group, or $R^5$ (or $R^6$) and $R^9$ (when q is not 0) or ($R^7$) are linked together through an alkylene group of 1–3 carbons or directly linked together, wherein the molar ration of endo-form (I-A) to exo-form (I-B) monomers ((I-A)/(I-B)) is from 80/20 to 0/100, wherein $X^1$ represents the portion wherein p, q, r and $R^1$ to $R^{15}$ are defined above, in the presence or absence of a hydrocarbon solvent and in the presence of a catalyst comprising an organoaluminum compound and a vanadium compound soluble in said hydrocarbon solvent or in said aromatic group-containing norbornene, until the resulting copolymer contains structural units derived from ethylene in an amount of 10 to 95 mol % and structural units derived from the aromatic group-containing norbornene in an amount of 90 to 5 mol %, and wherein the copolymer has an intrinsic viscosity (η), as measured in decalin at 135° C., of 0.05 to 10 dl/g, and wherein the structural units derived from the aromatic group-containing norbornene are represented by the following general formula (II):

wherein p, q and r and $R^1$ to $R^{15}$ are defined above.

6. The process according to claim 5 further comprising the step of contacting a norbornene isomer mixture containing an amount of endo-form (I-A) of not less than 85 mol % with a solid acid catalyst until the molar ratio of the endo-form (I-A) to the exo-form (I-B) becomes 80/20 to 0/100.

* * * * *